(12) United States Patent
Nieendick et al.

(10) Patent No.: US 7,176,171 B2
(45) Date of Patent: Feb. 13, 2007

(54) LOW-VISCOSITY OPACIFIERS WITHOUT ANIONIC SURFACE-ACTIVE AGENTS

(75) Inventors: Claus Nieendick, Krefeld (DE); Mirella Nalborczyk, Duesseldorf (DE); Josef Koester, Duesseldorf (DE); Anke Eggers, Duesseldorf (DE)

(73) Assignee: Cognis Deutschland GmbH & Co. KG, Duesseldorf (DE)

( * ) Notice: Subject to any disclaimer, the term of this patent is extended or adjusted under 35 U.S.C. 154(b) by 342 days.

(21) Appl. No.: 10/333,160

(22) PCT Filed: Jul. 7, 2001

(86) PCT No.: PCT/EP01/07819

§ 371 (c)(1),
(2), (4) Date: Jun. 9, 2003

(87) PCT Pub. No.: WO02/05781

PCT Pub. Date: Jan. 24, 2002

(65) Prior Publication Data

US 2004/0037793 A1 Feb. 26, 2004

(30) Foreign Application Priority Data

Jul. 17, 2000 (DE) ................ 100 34 619

(51) Int. Cl.
*C11D 1/90* (2006.01)
*C11D 3/22* (2006.01)
*A61K 8/40* (2006.01)
*A61K 8/73* (2006.01)
*A61K 8/92* (2006.01)

(52) U.S. Cl. ............ 510/123; 510/119; 510/222; 510/437; 510/474; 424/401; 424/493; 424/498; 424/499; 424/502; 424/70.13

(58) Field of Classification Search ........... 510/119, 510/123, 222, 437, 474; 424/401, 493, 498, 424/499, 502, 70.13
See application file for complete search history.

(56) References Cited

U.S. PATENT DOCUMENTS

| | | | |
|---|---|---|---|
| 4,172,887 A | 10/1979 | Vanlerberghe et al. | |
| 5,705,169 A | 1/1998 | Stein et al. | |
| 5,730,960 A | 3/1998 | Stein et al. | |
| 5,888,487 A * | 3/1999 | Baumoeller et al. | 424/70.1 |
| 5,945,091 A | 8/1999 | Habeck et al. | |
| 6,193,960 B1 | 2/2001 | Metzger et al. | |
| 6,641,803 B1 * | 11/2003 | Kahre et al. | 424/70.1 |

FOREIGN PATENT DOCUMENTS

| | | |
|---|---|---|
| DE | 1 165 574 | 3/1964 |
| DE | 2 024 051 | 12/1971 |
| DE | 195 11 572 | 10/1996 |
| DE | 19511572 A1 * | 10/1996 |
| DE | 197 12 033 | 9/1998 |
| DE | 197 28 084 | 1/1999 |
| DE | 197 56 377 | 6/1999 |
| EP | 0 510 870 | 10/1992 |
| EP | 0 693 471 | 1/1996 |
| EP | 0 694 521 | 1/1996 |
| EP | 0 818 450 | 1/1998 |
| EP | WO 99/39690 * | 8/1999 |
| FR | 2 252 840 | 8/1975 |
| GB | 962919 | 7/1964 |
| GB | 1 333 475 | 5/1970 |
| WO | 97/29170 | 8/1997 |
| WO | WO 97/29170 | 8/1997 |

OTHER PUBLICATIONS

Biermann, et al., "Alkylpolyglucoside—Technologie und Eigenschaften", Starch/Stärke, vol. 45, VCH Verlagsgesellschaft mbH, Weinheim, (1993), pp. 281-288, not translated.

Salka, "Alkyl Polyglycosides Properties and Applications", Cosmetics & Toiletries, vol. 108, (Mar. 1993), pp. 89-94.

J. Kahre, et al., "Alkylpolyglycoside-Ein neues Konzept für Pflege und Verträglich-keit in der Kosmetik", SÖFW-Journal, 121, (1995), pp. 598, 600-601, 604-611, not translated.

U. Ploog, "Kosmetika Aerosole Riechstoffe", Seifen-Öle-Fette-Wachse, vol. 198, (1982), pp. 373-376, not translated.

A.J. O'Lenick, et al., "Amphoteric Surfactants", HAPPI, (Nov. 1986), pp. 70-74, 125-126.

S. Holzman, et al., "Amphoteric Surfactants", Tenside Detergents, vol. 23, (1986), pp. 309-313.

R. Bilbo, et al., "Amphoteric Surfactants A Structure Function Study", Soap/Cosmetics/Chemical Specialties, (Apr. 1990), pp. 46, 48, 50, 114 & 116.

P.R. Ellis, et al., "Amphoteric Surfactants—The Next Generation", Euro Cosmetics, vol. 1, (1994), pp. 14-16.

Falbe, Surfactants in Consumer Products, Springer Verlag, Berlin, (1987), pp. 54-124.

Falbe, "Katalysatoren, Tenside und Mineralöladditive" (Catalysts, Surfactants and Mineral Oil Additives), Thieme Verlag, Stuttgart, (1978), pp. 123-217, not translated.

R. Lochhead, et al., "Encyclopedia of Polymers and Thickeners for Cosmetics", Cosmetics & Toiletries, vol. 108, (May 1993), pp. 95-114, 116-124, 127-130, 132-135.

P. Finkel, "Formulierung kosmetischer Sonnenschutzmittel", SÖFW-Journal, 122, (1996), pp. 543-546 & 548, not translated.

C. Todd, et al., "Volatile silicone fluids for cosmetic formulations", Cosmetics and Toiletries, vol. 91, (Jan. 1976), pp. 29-32.

(Continued)

*Primary Examiner*—Brian P Mruk
(74) *Attorney, Agent, or Firm*—John F. Daniels; Arthur G. Seifert

(57) ABSTRACT

An emulsifier mixture for use in a wax-based opacifier composition is comprised of: (a) an alkyl and/or alkenyl oligoglycoside; (b) a fatty acid partial glyceride and optionally (c) at least one amphoteric surfactant, with the proviso that the ratio by weight of (a) and optionally (c) to (b) is between 6:1 and 3:1 and wherein the composition is free from anionic surfactants.

10 Claims, No Drawings

OTHER PUBLICATIONS

P. Finkel, "Formulierung kosmetischer Sonnenschutzmittel", Parfümerie und Kosmetik, vol. 80, No. 3, (1999), pp. 10-12, 14-16, not translated.

"Kosmetische Färbemittel", Farbstoffkommission der Deutschen Forschungsgemeinschaft, Verlag Chemie, Weinheim, (1984), pp. 81-106, not translated.

* cited by examiner

LOW-VISCOSITY OPACIFIERS WITHOUT ANIONIC SURFACE-ACTIVE AGENTS

BACKGROUND OF THE INVENTION

This invention relates to opacifiers containing waxes, an emulsifier mixture of alkyl and/or alkenyl oligoglycosides, fatty acid partial glycerides and optionally amphoteric surfactants in a certain ratio by weight, but no anionic surfactants, and to their use as opacifiers.

In the formulation of a number of surface-active household products, such as dishwashing detergents for example, or cosmetic preparations, such as hair shampoos for example, particular importance is attributed to the products being clear and not clouding, even in storage. In other cases, cloudy products with a shimmering effect known as pearlescence are required for the same purpose. A third group of products is made with a non-shimmering opaque whiteness using so-called opacifiers.

Opacifiers are fine-particle dispersions of polymers or solids which, apart from water and/or a polyol (for example glycerol), largely contain only a wax and a suitable emulsifier. Known opacifiers are mainly based on copolymers based on acrylic or methacrylic acid and styrene and are not biodegradable. German patent DE 19511572 C2 describes low-viscosity opacifier concentrates based on waxes, sugar surfactants and partial glycerides. Although these concentrates are readily biodegradable, they have high viscosities and are in need of improvement so far as their particle fineness is concerned.

Accordingly, the problem addressed by the invention was to provide opacifier preparations or concentrates based on waxes which would be highly concentrated but which would have distinctly reduced mean particle sizes and lower viscosities by comparison with the prior art and would be biodegradable. In addition, the preparations according to the invention would produce more intense whiteness, but no pearlescence, in aqueous surfactant solutions and, by virtue of their particle size, would be sufficiently stable in storage, even at elevated temperatures. Also, the addition of amphoteric surfactants would have no effect on the stability of such preparations.

DESCRIPTION OF THE INVENTION

The present invention relates to wax-based opacifier preparations which are characterized in that they contain an emulsifier mixture of
(a) at least one alkyl and/or alkenyl oligoglycoside,
(b) at least one fatty acid partial glyceride and optionally
(c) at least one amphoteric surfactant, with the proviso that the ratio by weight of (a) and optionally (c) to (b) is between 6:1 and 3:1, preferably between 3.5:1 and 5:1 and more particularly between 4:1 and 4.7:1 and the preparations are free from anionic surfactants. In one particular embodiment of the invention, the ratio by weight of components (a) and optionally (c) to component (b) is between 5:1 and 1.5:1 and more particularly between 3:1 and 2:1.

It has surprisingly been found that mixtures based on waxes with alkyl oligoglycosides and partial glycerides in a selected ratio by weight give products which have a particularly small mean particle sizes by comparison with the prior art. Accordingly, the required white opaque effect is also intensified by these particularly fine-particle preparations and no pearlescence is formed. In addition, these products have particularly low viscosities, are biodegradable, show good flow and pumping properties and are sufficiently stable in storage. The products retain their stability and favorable properties in the presence of amphoteric surfactants, such as betaines for example. These advantageous properties can only be achieved for opacifier systems free from anionic surfactants.

Alkyl and/or Alkenyl Oligoglycosides

Alkyl and/or alkenyl oligoglycosides are known nonionic surfactants which correspond to formula (I):

$$R^1O\text{-}[G]_p \quad (I)$$

in which $R^1$ is an alkyl and/or alkenyl group containing 4 to 22 carbon atoms, G is a sugar unit containing 5 or 6 carbon atoms and p is a number of 1 to 10. They may be obtained by the relevant methods of preparative organic chemistry. The overviews presented by Bierman et al. in Starch/Stärke 45, 281 (1993), by B. Salka in Cosm. Toil. 108, 89 (1993) and by J. Kahre in SÖFW-Journal No. 8, 598 (1995) are cited as representative of the extensive literature available on this subject.

The alkyl and/or alkenyl oligoglycosides may be derived from aldoses or ketoses containing 5 or 6 carbon atoms, preferably glucose. Accordingly, the preferred alkyl and/or alkenyl oligoglycosides are alkyl and/or alkenyl oligoglucosides. The index p in general formula (I) indicates the degree of oligomerization (DP), i.e. the distribution of mono-and oligoglycosides, and is a number of 1 to 10. Whereas p in a given compound must always be an integer and, above all, may assume a value of 1 to 6, the value p for a certain alkyl oligoglycoside is an analytically determined calculated quantity which is generally a broken number. Alkyl and/or alkenyl oligoglycosides having an average degree of oligomerization p of 1.1 to 3.0 are preferably used. Alkyl and/or alkenyl oligoglycosides having a degree of oligomerization of less than 1.7 and, more particularly, between 1.2 and 1.4 are preferred from the applicational point of view. The alkyl or alkenyl radical $R^1$ may be derived from primary alcohols containing 4 to 11 and preferably 8 to 10 carbon atoms. Typical examples are butanol, caproic alcohol, caprylic alcohol, capric alcohol and undecyl alcohol and the technical mixtures thereof obtained, for example, in the hydrogenation of technical fatty acid methyl esters or in the hydrogenation of aldehydes from Roelen's oxosynthesis. Alkyl oligoglucosides having a chain length of $C_8$ to $C_{10}$ (DP=1 to 3), which are obtained as first runnings in the separation of technical $C_{8\text{-}18}$ coconut oil fatty alcohol by distillation and which may contain less than 6% by weight of $C_{12}$ alcohol as an impurity, and also alkyl oligoglucosides based on technical $C_{9/11}$ oxoalcohols (DP=1 to 3) are preferred. In addition, the alkyl or alkenyl radical $R^1$ may also be derived from primary alcohols containing 12 to 22 and preferably 12 to 14 carbon atoms. Typical examples are lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol and technical mixtures thereof which may be obtained as described above. Alkyl oligoglucosides based on hydrogenated $C_{12/14}$ coconut oil fatty alcohol having a DP of 1 to 3 are preferred.

The preparations according to the invention may contain the alkyl and/or alkenyl oligoglycosides in quantities of 0.1 to 20, preferably 5 to 18 and more particularly 8 to 13% by weight, based on the final composition.

Fatty Acid Partial Glycerides

Fatty acid partial glycerides, i.e. monoglycerides, diglycerides and technical mixtures thereof may still contain small quantities of di- and triglycerides from their production. The partial glycerides preferably correspond to formula (II):

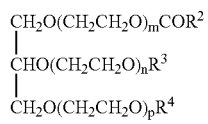

(II)

in which $R^2CO$ is a linear or branched, saturated and/or unsaturated acyl group containing 6 to 22 and preferably 12 to 18 carbon atoms, $R^3$ and $R^4$ independently of one another have the same meaning as $R^2CO$ or represent OH and the sum (m+n+p) is 0 or a number of 1 to 100 and preferably 5 to 25, with the proviso that at least one of the two substituents $R^3$ and $R^4$ represents OH. Typical examples are mono- and/or diglycerides based on caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and technical mixtures thereof. Technical lauric acid glycerides, palmitic acid glycerides, stearic acid glycerides, isostearic acid glycerides, oleic acid glycerides, behenic acid glycerides and/or erucic acid glycerides which have a monoglyceride content of 50 to 95% by weight and preferably 60 to 90% by weight are preferably used. Relatively long-chain partial glycerides, for example based on oleic acid or stearic acid, especially mixtures of glycerides based on saturated and unsaturated fatty acids, are particularly suitable.

The preparations according to the invention may contain the fatty acid partial glycerides in quantities of 0.1 to 5, preferably 1 to 3.5 and more particularly 1.2 to 2.4% by weight, based on the final composition.

Amphoteric Surfactants

The preparations according to the invention may optionally contain amphoteric surfactants such as, for example, alkyl betaines, alkyl amidobetaines, aminopropionates, aminoglycinates, imidazolinium betaines and sulfobetaines. Betaines are preferably used. Betaines are known surfactants which are mainly produced by carboxyalkylation, preferably carboxymethylation, of aminic compounds. The starting materials are preferably condensed with halocarboxylic acids or salts thereof, more particularly with sodium chloroacetate, 1 mol of salt being formed per mol of betaine. The addition of unsaturated carboxylic acids, for example acrylic acid, is also possible. Particulars of the nomenclature and, in particular, the distinction between betaines and "genuine" amphoteric surfactants can be found in the article by U. Ploog in Seifen-Öle-Fette-Wachse, 198, 373 (1982). Other reviews of this subject have been published, for example, by A. O'Lenick et al. in HAPPI, Nov. 70 (1986), by S. Holzman et al. in Tens. Surf. Det. 23, 309 (1986), by R. Bibo et al. in Soap Cosm. Chem. Spec., Apr. 46 (1990) and by P. Ellis et al. in Euro Cosm. 1, 14 (1994). Examples of suitable betaines are the carboxyalkylation products of secondary and, in particular, tertiary amines corresponding to formula (III):

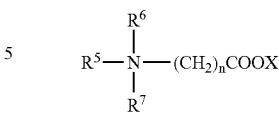

(III)

in which $R^5$ stands for alkyl and/or alkenyl groups containing 6 to 22 carbon atoms, $R^6$ stands for hydrogen or alkyl groups containing 1 to 4 carbon atoms, $R^7$ stands for alkyl groups containing 1 to 4 carbon atoms, n is a number of 1 to 6 and X is an alkali metal and/or alkaline earth metal or ammonium. Typical examples are the carboxymethylation products of hexyl methyl amine, hexyl dimethyl amine, octyl dimethyl amine, decyl dimethyl amine, dodecyl methyl amine, dodecyl dimethyl amine, dodecyl ethyl methyl amine, $C_{12/14}$ cocoalkyl dimethyl amine, myristyl dimethyl amine, cetyl dimethyl amine, stearyl dimethyl amine, stearyl ethyl methyl amine, oleyl dimethyl amine, $C_{16/18}$ tallow alkyl dimethyl amine and technical mixtures thereof.

Other suitable betaines are carboxyalkylation products of amido-amines corresponding to formula (IV):

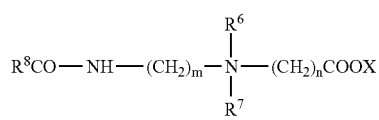

(IV)

in which $R^8CO$ is an aliphatic acyl group containing 6 to 22 carbon atoms and 0 or 1 to 3 double bonds, m is a number of 1 to 3 and $R^6$, $R^7$, n and X are as defined above. Typical examples are reaction products of fatty acids containing 6 to 22 carbon atoms, namely caproic acid, caprylic acid, capric acid, lauric acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and technical mixtures thereof, with N,N-dimethyl aminoethyl amine, N,N-dimethyl aminopropyl amine, N,N-diethyl aminoethyl amine and N,N-diethyl aminopropyl amine which are condensed with sodium chloroacetate. It is preferred to use a condensation product of $C_{8/18}$ cocofatty acid-N,N-dimethyl aminopropyl amide with sodium chloroacetate.

Other suitable starting materials for the betaines to be used in accordance with the invention are imidazolines corresponding to formula (V):

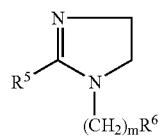

(V)

in which $R^5$ is an alkyl group containing 5 to 21 carbon atoms, $R^6$ is a hydroxyl group, an $OCOR^5$ or $NHCOR^5$ group and m=2 or 3. Imidazolines are also known compounds which may be obtained, for example, by cyclizing condensation of 1 or 2 mol of fatty acid with polyfunctional amines, for example aminoethyl ethanolamine (AEEA) or diethylene triamine. The corresponding carboxyalkylation products are mixtures of different open-chain betaines. Typical examples are condensation products of the above-mentioned fatty acids with AEEA, preferably imidazolines based on lauric acid or—again—$C_{12/14}$ cocofatty acid which are subsequently betainized with sodium chloroacetate.

The preparations according to the invention may contain the amphoteric surfactants in quantities of 0 to 10, preferablyh 1 to 5 and more particularly 2 to 4% by weight, based on the final composition.

Waxes

Basically, the choice of the waxes is not critical. Typical examples are alkylene glycol fatty acid esters, wax esters, hydrogenated triglycerides, saturated fatty alcohols containing 16 to 18 carbon atoms, ethylene oxide adducts with $C_{16-18}$ fatty acids and/or paraffin waxes.

Alkylene Glycol Fatty Acid Esters

In another preferred embodiment of the invention, the waxes used are alkylene glycol fatty acid esters corresponding to formula (VI):

$$R^9CO—O-[A]-O—R^{10} \qquad (VI)$$

in which $R^9CO$ is an aliphatic acyl group containing 6 to 22 carbon atoms and 0 and/or 1, 2 or 3 double bonds, $R^{10}$ has the same meaning as $R^9CO$ or is a hydroxyl group and A is a linear or branched, optionally hydroxysubstituted alkylene group containing 2 to 5 carbon atoms.

These waxes are preferably esters of ethylene glycol or propylene glycol with caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and technical mixtures thereof. The use of ethylene glycol distearate is particularly preferred.

The preparations according to the invention may contain the waxes, preferably alkylene glycol fatty acid esters, in quantities of 10 to 35, preferably 12 to 28 and more particularly 15 to 25% by weight, based on the final composition.

Commercial Applications

The opacifier preparations according to the invention have a solids content of preferably 20 to 45, more preferably 30 to 41 and most preferably 35 to 37% by weight, based on the final composition. Accordingly, the present invention also relates to their use as opacifiers, preferably in cosmetic preparations.

They are distinguished by low viscosities, preferably in the range from 2,000 to 6,000 mPas and more particularly in the range from 2,500 to 5,000 mPas (Brookfield: 23° C., spindle 5, 10 r.p.m.), by good flow and pumping properties and by particular particle fineness of the crystals in the dispersion. The particular particle fineness is produced by a particle size distribution where at least 85, preferably 90, more preferably 95 and most preferably 99.9% of the particles have a diameter of <15 μm. The mean particle diameter is preferably <15, more preferably <10 and most preferably <7 μm.

Another advantage of the opacifier preparations according to the invention is their high stability to sedimentation in the event of prolonged storage. When used in quantities of 0.1 to 12, preferably 0.5 to 6 and more particularly 1 to 3.5% by weight in aqueous surface-active compositions, such as manual detergents for example, or in cosmetic and/or pharmaceutical preparations, such as for example hair shampoos, hair lotions, foam baths, shower baths, oral and dental care products, creams, gels, lotions, aqueous/alcoholic solutions, emulsions and the like, the opacifier preparations according to the invention produce a permanent, uniform and—compared with the prior art—particularly intensive white opaqueness without any pearlescence.

The choice of the surfactants in aqueous solutions of which the preparations according to the invention produce a white opaqueness is very important because the addition of anionic surfactants produces a distinct increase in viscosity and the required particle fineness and hence the particularly intensive white opaqueness fail to appear. Instead pearlescence is generally produced because relatively large particles are also present through the use of anionic surfactants. Accordingly, the opacifiers can only be used in aqueous solutions of nonionic and/or amphoteric or zwitterionic surfactants. They are preferably used in aqueous solutions containing amphoteric or zwitterionic surfactants.

The surfactant mixtures according to the invention may additionally contain other surfactants, oil components, emulsifiers, pearlizing waxes, consistency factors, thickeners, superfatting agents, stabilizers, polymers, silicone compounds, fats, waxes, lecithins, phospholipids, biogenic agents, UV protection factors, antioxidants, deodorants, antiperspirants, antidandruff agents, film formers, swelling agents, insect repellents, self-tanning agents, tyrosine inhibitors (depigmenting agents), hydrotropes, solubilizers, preservatives, perfume oils, dyes and the like as further auxiliaries and additives.

Surfactants

Nonionic and/or cationic surfactants may be present as surfactants. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partly oxidized glucuronic acid derivatives, fatty acid-N-alkyl glucamides, protein hydrolyzates (particularly wheat-based vegetable products), polyol fatty acid esters, sugar esters, sorbitan esters, polysorbates and amine oxides. If the nonionic surfactants contain polyglycol ether chains, they may have a conventional homolog distribution, although they preferably have a narrow-range homolog distribution. Typical examples of cationic surfactants are quaternary ammonium compounds, for example dimethyl distearyl ammonium chloride, and esterquats, more particularly quaternized fatty acid trialkanolamine ester salts. The surfactants mentioned are all known compounds. Information on their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside und Mineralöladditive (Catalysts, Surfactants and Mineral Oil Additives)", Thieme Verlag, Stuttgart, 1978, pages 123–217.

Oil Components

Suitable oil components are, for example, Guerbet alcohols based on fatty alcohols containing 6 to 18 and preferably 8 to 10 carbon atoms, esters of linear $C_{6-22}$ fatty acids with linear or branched $C_{6-22}$ fatty alcohols or esters of branched $C_{6-13}$ carboxylic acids with linear or branched $C_{6-22}$ fatty alcohols such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_{6-22}$ fatty acids with branched alcohols, more particularly 2-ethyl hexanol, esters of $C_{18-38}$ alkyl hydroxycarboxylic acids with linear or branched $C_{6-22}$ fatty alcohols (cf. DE 19756377 A1), more especially Dioctyl Malate, esters of linear and/or branched fatty acids with polyhydric alcohols (for example propylene glycol, dimer diol or trimer triol) and/or Guerbet alcohols, triglycerides based on $C_{6-10}$ fatty acids, liquid mono-/di-/triglyceride mixtures based on $C_{6-18}$ fatty acids (cf. EP 97/00434), esters of $C_{6-22}$ fatty alcohols and/or Guerbet alcohols with aromatic carboxylic acids, more particularly benzoic acid, esters of $C_{6-22}$ dicarboxylic acids with linear or branched alcohols containing 1 to 22 carbon atoms or polyols containing 2 to 10 carbon atoms and 2 to 6 hydroxyl groups, vegetable oils, branched primary alcohols, substituted cyclohexanes, linear and branched $C_{6-22}$ fatty alcohol carbonates, for example Dicaprylyl Carbonate (Cetiol® CC), Guerbet carbonates based on $C_{6-18}$ and preferaly $C_{8-10}$ fatty alcohols, esters of benzoic acid with linear and/or branched $C_{6-22}$ alcohols (for example Finsolv® TN), linear or branched, symmetrical or nonsymmetrical dialkyl ethers containing 6 to 22 carbon atoms per alkyl group, for example Dicaprylyl Ether (Cetiol® OE), ring opening products of epoxidized fatty acid esters with polyols, silicone oils (cyclomethicone, silicon methicones) and/or aliphatic or naphthenic hydrocarbons, for example squalane, squalene or dialkyl cyclohexanes.

Emulsifiers

Suitable emulsifiers are, for example, nonionic surfactants from at least one of the following groups:
 products of the addition of 2 to 30 mol ethylene oxide and/or 0 to 5 mol propylene oxide onto linear $C_{8-22}$ fatty alcohols, $C_{12-22}$ fatty acids and alkyl phenols containing 8 to 15 carbon atoms in the alkyl group and alkylamines containing 8 to 22 carbon atoms in the alkyl group;
 alkyl and/or alkenyl oligoglycosides containing 8 to 22 carbon atoms in the alk(en)yl group and ethoxylated analogs thereof;
 products of the addition of 1 to 15 mol ethylene oxide onto castor oil and/or hydrogenated castor oil;
 products of the addition of 15 to 60 mol ethylene oxide onto castor oil and/or hydrogenated castor oil;
 partial esters of sorbitan with unsaturated, linear or saturated, branched fatty acids containing 12 to 22 carbon atoms and/or hydroxycarboxylic acids containing 3 to 18 carbon atoms and addition products thereof with 1 to 30 mol ethylene oxide;
 partial esters of polyglycerol (average degree of self-condensation 2 to 8), trimethylolpropane, pentaerythritol, sugar alcohols (for example sorbitol), alkyl glucosides (for example methyl glucoside, butyl glucoside, lauryl glucoside) and polyglucosides (for example cellulose) with saturated and/or unsaturated, linear or branched fatty acids containing 12 to 22 carbon atoms and/or hydroxycarboxylic acids containing 3 to 18 carbon atoms and addition products thereof with 1 to 30 mol ethylene oxide;
 mixed esters of pentaerythritol, fatty acids, citric acid and fatty alcohol according to DE 1165574 PS and/or mixed esters of fatty acids containing 6 to 22 carbon atoms, methyl glucose and polyols, preferably glycerol or polyglycerol,
 mono-, di- and trialkyl phosphates and mono-, di- and/or tri-PEG-alkyl phosphates and salts thereof,
 wool wax alcohols,
 polysiloxane/polyalkyl/polyether copolymers and corresponding derivatives,
 block copolymers, for example Polyethylene Glycol-30 Dipolyhydroxystearate;
 polymer emulsifiers, for example Pemulen types (TR-1, TR-2) from Goodrich;
 polyalkylene glycols and
 glycerol carbonate.

The addition products of ethylene oxide and/or propylene oxide onto fatty alcohols, fatty acids, alkylphenols or castor oil are known commercially available products. They are homolog mixtures of which the average degree of alkoxylation corresponds to the ratio between the quantities of ethylene oxide and/or propylene oxide and substrate with which the addition reaction is carried out. $C_{12-18}$ fatty acid monoesters and diesters of addition products of ethylene oxide onto glycerol are known as refatting agents for cosmetic formulations from DE 2024051 PS.

Alkyl and alkenyl oligoglycosides, their production and their use are known from the prior art. They are produced in particular by reacting glucose or oligosaccharides with primary $C_{8-18}$ alcohols. So far as the glycoside unit is concerned, both monoglycosides where a cyclic sugar unit is attached to the fatty alcohol by a glycoside bond and oligomeric glycosides with a degree of oligomerization of preferably up to about 8 are suitable. The degree of oligomerization is a statistical mean value to which the homolog distribution typical of such technical products corresponds.

Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof which may still contain small quantities of triglyceride from the production process. Addition products of 1 to 30 and preferably 5 to 10 mol ethylene oxide onto the partial glycerides mentioned are also suitable.

Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 moles of ethylene oxide onto the sorbitan esters mentioned are also suitable.

Typical examples of suitable polyglycerol esters are Polyglyceryl-2 Dipolyhydroxystearate (Dehymuls® PGPH), Polyglycerin-3-Diisostearate (Lameform® TGI), Polyglyceryl-4 Isostearate (Isolan® GI 34), Polyglyceryl-3 Oleate, Diisostearoyl Polyglyceryl-3 Diisostearate (Isolan® PDI), Polyglyceryl-3 Methylglucose Distearate (Tego Care® 450), Polyglyceryl-3 Beeswax (Cera Bellina®), Polyglyceryl-4 Caprate (Polyglycerol Caprate T2010/90), Polyglyceryl-3 Cetyl Ether (Chimexane® NL), Polyglyceryl-3 Distearate (Cremophor® GS 32) and Polyglyceryl Polyricinoleate (Admul® WOL 1403), Polyglyceryl Dimerate Isostearate and mixtures thereof. Examples of other suitable polyesters are the mono-, di- and triesters of trimethylol propane or pentaerythritol with lauric acid, cocofatty acid, tallow fatty acid, palmitic acid, stearic acid, oleic acid, behenic acid and the like optionally reacted with 1 to 30 mol ethylene oxide.

Other suitable emulsifiers are zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine. Finally, cationic surfactants are also suitable emulsifiers, those of the esterquat type, preferably methyl-quaternized difatty acid triethanolamine ester salts, being particularly preferred.

Fats and Waxes

Typical examples of fats are glycerides, i.e. solid or liquid, vegetable or animal products which consist essentially of mixed glycerol esters of higher fatty acids. Suitable waxes are inter alia natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes and microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes. Besides the fats, other suitable additives are fat-like substances, such as lecithins and phospholipids. Lecithins are known among experts as glycerophospholipids which are formed from fatty acids, glycerol, phosphoric acid and choline by esterification. Accordingly, lecithins are also frequently referred to by experts as phosphatidyl cholines (PCs) and correspond to the following general formula:

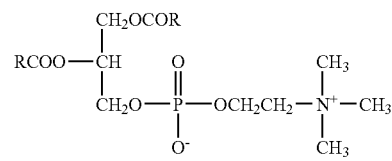

where R typically represents linear aliphatic hydrocarbon radicals containing 15 to 17 carbon atoms and up to 4 cis-double bonds. Examples of natural lecithins are the kephalins which are also known as phosphatidic acids and which are derivatives of 1,2-diacyl-sn-glycerol-3-phosphoric acids. By contrast, phospholipids are generally understood to be mono- and preferably diesters of phosphoric acid with glycerol (glycerophosphates) which are normally classed as fats. Sphingosines and sphingolipids are also suitable.

Pearlizing Waxes

Suitable pearlizing waxes are, for example, alkylene glycol esters, especially ethylene glycol distearate; fatty acid alkanolamides, especially coconutfatty acid diethanolamide; partial glycerides, especially stearic acid monoglyceride; esters of polybasic, optionally hydroxysubstituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

Consistency Factors and Thickeners

The consistency factors mainly used are fatty alcohols or hydroxyfatty alcohols containing 12 to 22 and preferably 16 to 18 carbon atoms and in addition partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used. Suitable thickeners are, for example, Aerosil types (hydrophilic silicas), polysaccharides, more especially xanthan gum, guarguar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® and Pemulens [Goodrich] or Synthalens® [Sigma]; Keltrols from Kelco; Sepigels from Seppic; Salcares from Allied Colloids), polyacrylamides, polymers, polyvinyl alcohol and polyvinyl pyrrolidone, surfactants such as, for example, ethoxylated fatty acid glycerides esters of fatty acids with polyols, for example pentaerythritol or trimethylol propane, narrow-range fatty alcohol ethoxylates or alkyl oligoglucosides and electrolytes, such as sodium chloride and ammonium chloride.

Superfatting Agents

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

Stabilizers

Metal salts of fatty acids such as, for example, magnesium, aluminium and/or zinc stearate or ricinoleate may be used as stabilizers.

Polymers

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grünau), quaternized wheat polypeptides, polyethyleneimine, cationic silicone polymers such as, for example, Amodimethicone, copolymers of adipic acid and dimethylamino-hydroxypropyl diethylenetriamine (Cartaretine®, Sandoz), copolymers of acrylic acid with dimethyl diallyl ammonium chloride (Merquat® 550, Chemviron), polyaminopolyamides as described, for example, in FR 2252840 A and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bis-dimethylamino-1, 3-propane, cationic guar gum such as, for example, Jaguar®CBS, Jaguar®C-17, Jaguar®C-16 of Celanese, quaternized ammonium salt polymers such as, for example, Mirapol® A-15, Mirapol® AD-1, Mirapol® AZ-1 of Miranol.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones. Other suitable polymers and thickeners can be found in Cosmetics & Toiletries, Vol. 108, May 1993, pages 95 et seq.

Silicone Compounds

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones, which are mixtures of dimethicones with an average chain length of 200 to 300 dimethylsiloxane units and hydrogenated silicates. A detailed overview of suitable volatile silicones can be found in Todd et al. in Cosm. Toil. 91, 27 (1976).

UV Protection Factors and Antioxidants

UV protection factors in the context of the invention are, for example, organic substances (light filters) which are liquid or crystalline at room temperature and which are capable of absorbing ultraviolet or infrared radiation and of releasing the energy absorbed in the form of longer-wave radiation, for example heat. UV-B filters can be oil-soluble or water-soluble. The following are examples of oil-soluble substances:

3-benzylidene camphor or 3-benzylidene norcamphor and derivatives thereof, for example 3-(4-methylbenzylidene)-camphor as described in EP 0693471 B1;

4-aminobenzoic acid derivatives, preferably 4-(dimethylamino)-benzoic acid-2-ethylhexyl ester, 4-(dimethylamino)-benzoic acid-2-octyl ester and 4-(dimethylamino)-benzoic acid amyl ester;

esters of cinnamic acid, preferably 4-methoxycinnamic acid-2-ethylhexyl ester, 4-methoxycinnamic acid propyl ester, 4-methoxycinnamic acid isoamyl ester, 2-cyano-3,3-phenylcinnamic acid-2-ethylhexyl ester (Octocrylene);

esters of salicylic acid, preferably salicylic acid-2-ethylhexyl ester, salicylic acid-4-isopropylbenzyl ester, salicylic acid homomenthyl ester;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzalmalonic acid, preferably 4-methoxybenzalmalonic acid di-2-ethylhexyl ester;

triazine derivatives such as, for example, 2,4,6-trianilino-(p-carbo-2'ethyl-1'-hexyloxy)-1,3,5-triazine and Octyl Triazone as described in EP 0818450 A1 or Dioctyl Butamido Triazone (Uvasorb® HEB);

propane-1,3-diones such as, for example, 1-(4-tert.butylphenyl)-3-(4'-methoxyphenyl)-propane-1,3-dione;

ketotricyclo(5.2.1.0)decane derivatives as described in EP 0694521 B1.

Suitable water-soluble substances are 2-phenylbenzimidazole-5-sulfonic acid and alkali metal, alkaline earth metal, ammonium, alkylammonium, alkanolammonium and glucammonium salts thereof;

sulfonic acid derivatives of benzophenones, preferably 2-hydroxy-4-methoxybenzophenone-5-sulfonic acid and salts thereof;

sulfonic acid derivatives of 3-benzylidene camphor such as, for example, 4-(2-oxo-3-bornylidenemethyl)-benzene sulfonic acid and 2-methyl-5-(2-oxo-3-bornylidene)-sulfonic acid and salts thereof.

Typical UV-A filters are, in particular, derivatives of benzoyl methane such as, for example, 1-(4'-tert.butylphenyl)-3-(4'-methoxyphenyl)-propane-1,3-dione, 4-tert.butyl-4'-methoxydibenzoyl methane (Parsol® 1789) or 1-phenyl-3-(4'-isopropylphenyl)-propane-1,3-dione and the eneamine compounds described in DE 19712033 A1 (BASF). The UV-A and UV-B filters may of course also be used in the form of mixtures. Particularly favorable combinations consist of the derivatives of benzoylmethane, for example 4-tert.-butyl-4'-methoxydibenzoyl methane (Parsol® 1789) and 2-cyano-3,3-phenylcinnamic acid-2-ethylhexyl ester (Octocrylene) in combination with esters of cinnamic acid, preferably 4-methoxycinnamic acid-2-ethylhexyl ester and/or 4-methoxycinnamic acid propyl ester and/or 4-methoxycinnamic acid isoamyl ester. These combinations are advantageously combined with water-soluble filters such as, for example, 2-phenylbenzimidazole-5-sufonic acid and alkali metal, alkaline earth metal, ammonium, alkylammonium, alkanolammonium and glucammonium salts.

Besides the soluble substances mentioned, insoluble light-blocking pigments, i.e. finely dispersed metal oxides or salts, may also be used for this purpose. Examples of suitable metal oxides are, in particular, zinc oxide and titanium dioxide and also oxides of iron, zirconium oxide, silicon, manganese, aluminium and cerium and mixtures thereof. Silicates (talcum), barium sulfate and zinc stearate may be used as salts. The oxides and salts are used in the form of the pigments for skin-care and skin-protecting emulsions and decorative cosmetics. The particles should have a mean diameter of less than 100 nm, preferably between 5 and 50 nm and more preferably between 15 and 30 nm. They may be spherical in shape although ellipsoidal particles or other non-spherical particles may also be used. The pigments may also be surface-treated, i.e. hydrophilicized or hydrophobicized. Typical examples are coated titanium dioxides, for example Titandioxid T 805 (Degussa) and Eusolex® T2000 (Merck). Suitable hydrophobic coating materials are, above all, silicones and, among these, especially trialkoxyoctylsilanes or simethicones. So-called micro- or nanopigments are preferably used in sun protection products. Micronized zinc oxide is preferably used. Other suitable UV filters can be found in P. Finkel's review in SÖFW-Journal 122, 543 (1996) and in Parfümerie und Kosmetik 3 (1999), pages 11 et seq.

Besides the two groups of primary sun protection factors mentioned above, secondary sun protection factors of the antioxidant type may also be used. Secondary sun protection factors of the antioxidant type interrupt the photochemical reaction chain which is initiated when UV rays penetrate into the skin. Typical examples are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages (for example pmole to μmole/kg), also (metal) chelators (for example α-hydroxyfatty acids, palmitic acid, phytic acid, lactoferrine), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example γ-linolenic acid, linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, α-glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, Superoxid-Dismutase, zinc and derivatives thereof (for example ZnO, $ZnSO_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

Biogenic Agents

In the context of the invention, biogenic agents are, for example, tocopherol, tocopherol acetate, tocopherol palmitate, ascorbic acid, retinol, bisabolol, allantoin, phytantriol, panthenol, AHA acids, amino acids, ceramides, pseudoceramides, essential oils, plant extracts and vitamin complexes.

Deodorants and Germ Inhibitors

Cosmetic deodorants counteract, mask or eliminate body odors. Body odors are formed through the action of skin bacteria on apocrine perspiration which results in the formation of unpleasant-smelling degradation products. Accordingly, deodorants contain active principles which act as germ inhibitors, enzyme inhibitors, odor absorbers or odor maskers. Basically, suitable germ inhibitors are any substances which act against gram-positive bacteria such as, for example, 4-hydroxybenzoic acid and salts and esters thereof, N-(4-chlorophenyl)-N'-(3,4-dichlorophenyl)urea, 2,4,4'-trichloro-2'-hydroxydiphenylether (triclosan), 4-chloro-3,5-dimethylphenol, 2,2'-methylene-bis-(6-bromo-4-chlorophenol), 3-methyl-4(1-methylethyl)-phenol, 2-benzyl-4-chlorophenol, 3-(4-chlorophenoxy)propane-1,2-diol, 3-iodo-2-propinyl butyl carbamate, chlorhexidine, 3,4,4'-trichlorocarbanilide (TTC), antibacterial perfumes, thymol, thyme oil, eugenol, clove oil, menthol, mint oil, farnesol, phenoxyethanol, glycerol monocaprate, glycerol monocaprylate, glycerol monolaurate (GML), diglycerol monocaprate (DMC), salicylic acid-N-alkylamides such as, for example, salicylic acid-n-octyl amide or salicylic acid-n-decyl amide.

Suitable enzyme inhibitors are, for example, esterase inhibitors. Esterase inhibitors are preferably trialkyl citrates, such as trimethyl citrate, tripropyl citrate, triisopropyl citrate, tributyl citrate and, in particular, triethyl citrate (Hydagen® CAT, Henkel KGaA, Dusseldorf/FRG). Esterase inhibitors inhibit enzyme activity and thus reduce odor formation. Other esterase inhibitors are sterol sulfates or phosphates such as, for example, lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester, hydroxycarboxylic acids and esters thereof, for example citric acid, malic acid, tartaric acid or tartaric acid diethyl ester, and zinc glycinate.

Suitable odor absorbers are substances which are capable of absorbing and largely retaining the odor-forming compounds. They reduce the partial pressure of the individual components and thus also reduce the rate at which they spread. An important requirement in this regard is that perfumes must remain unimpaired. Odor absorbers are not active against bacteria. They contain, for example, a complex zinc salt of ricinoleic acid or special perfumes of largely neutral odor known to the expert as "fixateurs" such as, for example, extracts of ladanum or styrax or certain abietic acid derivatives as their principal component. Odor maskers are perfumes or perfume oils which, besides their odor-masking function, impart their particular perfume note to the deodorants. Suitable perfume oils are, for example, mixtures of natural and synthetic fragrances. Natural fragrances include the extracts of blossoms, stems and leaves, fruits, fruit peel, roots, woods, herbs and grasses, needles and branches, resins and balsams. Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, p-tert.butyl cyclohexylacetate, linalyl acetate, phenyl ethyl acetate, linalyl benzoate, benzyl formate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxy-citronellal, lilial and bourgeonal. Examples of suitable ketones are the ionones and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable fragrance. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetivert oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, ahexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Antiperspirants reduce perspiration and thus counteract underarm wetness and body odor by influencing the activity of the eccrine sweat glands. Aqueous or water-free antiperspirant formulations typically contain the following ingredients:
astringent active principles,
oil components,
nonionic emulsifiers,
co-emulsifiers,
consistency factors,
auxiliaries in the form of, for example, thickeners or complexing agents and/or
non-aqueous solvents such as, for example, ethanol, propylene glycol and/or glycerol.

Suitable astringent active principles of antiperspirants are, above all, salts of aluminium, zirconium or zinc. Suitable antihydrotic agents of this type are, for example, aluminium chloride, aluminium chlorohydrate, aluminium dichlorohydrate, aluminium sesquichlorohydrate and complex compounds thereof, for example with 1,2-propylene glycol, aluminium hydroxyallantoinate, aluminium chloride tartrate, aluminium zirconium trichlorohydrate, aluminium zirconium tetrachlorohydrate, aluminium zirconium pentachlorohydrate and complex compounds thereof, for example with amino acids, such as glycine. Oil-soluble and water-soluble auxiliaries typically encountered in antiperspirants may also be present in relatively small amounts. Oil-soluble auxiliaries such as these include, for example,
inflammation-inhibiting, skin-protecting or pleasant-smelling essential oils,
synthetic skin-protecting agents and/or
oil-soluble perfume oils.

Typical water-soluble additives are, for example, preservatives, water-soluble perfumes, pH regulators, for example buffer mixtures, water-soluble thickeners, for example water-soluble natural or synthetic polymers such as, for example, xanthan gum, hydroxyethyl cellulose, polyvinyl pyrrolidone or high molecular weight polyethylene oxides.

Film Formers

Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds.

Antidandruff Agents

Suitable antidandruff agents are Pirocton Olamin (1-hydroxy-4-methyl-6-(2,4,4-trimethylpentyl)-2-(1H)-pyridinone monoethanolamine salt), Baypival® (Climbazole), Ketoconazol® (4-acetyl-1-{4-[2-(2,4-dichlorophenyl) r-2-(1H-imidazol-1-ylmethyl)-1,3-dioxylan-c-4-ylmethoxyphenyl}-piperazine, ketoconazole, elubiol, selenium disulfide, colloidal sulfur, sulfur polyethylene glycol sorbitan monooleate, sulfur ricinol polyethoxylate, sulfur tar distillate, salicylic acid (or in combination with hexachlorophene), undecylenic acid, monoethanolamide sulfosuccinate Na salt, Lamepon® UD (protein/undecylenic acid condensate), zinc pyrithione, aluminium pyrithione and magnesium pyrithione/dipyrithione magnesium sulfate.

Swelling Agents

Suitable swelling agents for aqueous phases are montmorillonites, clay minerals, Pemulen and alkyl-modified Carbopol types (Goodrich). Other suitable polymers and swelling agents can be found in R. Lochhead=s review in Cosm. Toil. 108, 95 (1993).

Insect Repellents

Suitable insect repellents are N,N-diethyl-m-toluamide, pentane-1,2-diol or Ethyl Butylacetylaminopropionate.

Self-tanning Agents and Depiqmenting Agents

A suitable self-tanning agent is dihydroxyacetone. Suitable tyrosine inhibitors which prevent the formation of melanin and are used in depigmenting agents are, for example, arbutin, koji acid, coumaric acid and ascorbic acid (vitamin C).

Hydrotropes

In addition, hydrotropes, for example ethanol, isopropyl alcohol or polyols, may be used to improve flow behavior. Suitable polyols preferably contain 2 to 15 carbon atoms and at least two hydroxyl groups. The polyols may contain other functional groups, more especially amino groups, or may be modified with nitrogen. Typical examples are
glycerol;
alkylene glycols such as, for example, ethylene glycol, diethylene glycol, propylene glycol, butylene glycol, hexylene glycol and polyethylene glycols with an average molecular weight of 100 to 1000 dalton;

technical oligoglycerol mixtures with a degree of self-condensation of 1.5 to 10 such as, for example, technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms, for example sorbitol or mannitol, sugars containing 5 to 12 carbon atoms, for example glucose or sucrose;

amino sugars, for example glucamine;

dialcoholamines, such as diethanolamine or 2-aminopropane-1,3-diol.

Preservatives

Suitable preservatives are, for example, phenoxyethanol, formaldehyde solution, parabens, pentanediol or sorbic acid and the other classes of compounds listed in Appendix 6, Parts A and B of the Kosm tikverordnung ("Cosmetics Directive").

Perfume Oils

Suitable perfume oils are mixtures of natural and synthetic perfumes. Natural perfumes include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamom, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, α-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable fragrance. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Dyes

Suitable dyes are any of the substances suitable and approved for cosmetic purposes as listed, for example, in the publication "Kosmetische Färbemittel" of the Farbstoffkommission der Deutschen Forschungs-gemeinschaft, Verlag Chemie, Weinheim, 1984, pages 81 to 106. These dyes are normally used in concentrations of 0.001 to 0.1% by weight, based on the mixture as a whole.

The total percentage content of auxiliaries and additives may be from 1 to 50% by weight and is preferably from 5 to 40% by weight, based on the particular formulation. The preparations may be produced by standard hot or cold processes and are preferably produced by the phase inversion temperature method.

EXAMPLES

The wax, the partial glycerides (b) and the various surfactants (a) were mixed in various ratios by weight and the particle fineness was determined by determining the particle size distribution in μm and the mean particle diameter in μm by laser diffraction (Mastersizer 2000; see product specification of MALVERN INSTRUMENTS GmbH, Herrenberg, Germany). Viscosity was measured by the Brookfield method (23° C., spindle 5, 10 r.p.m., mPas). The results are set out in Table 1.

TABLE 1

| Cosmetic preparations (quantities in % by weight active substance, based on the final composition) | | | | | | | | |
|---|---|---|---|---|---|---|---|---|
| Composition (INCI) | 1 | 2 | 3 | 4 | C1 | C2 | C3 | C4 |
| Cutina ® AGS Ethyleneglycol Distearate | 25 | 25 | 25 | 25 | 25 | 25 | 25 | 25 |
| Plantacare 818 ® Coca Glucoside | 9.1 | 9.1 | 9.1 | 9.1 | 9.1 | 9.1 | 9.1 | 9.1 |
| Dehyton ® K Cocoamidopropyl Betaine | — | — | 2.7 | — | — | 2.7 | — | — |
| Monomuls ® 90-O18 Glyceryl Oleate | — | 1.8 | 2.5 | 1.25 | — | — | 0.45 | — |
| Monomuls ® 90-L12 Glyceryl Laurate | 2.5 | — | — | — | 0.9 | 0.9 | — | 2.5 |

TABLE 1-continued

| Composition (INCI) | 1 | 2 | 3 | 4 | C1 | C2 | C3 | C4 |
|---|---|---|---|---|---|---|---|---|
| Cutina ® GMS Glyceryl Stearate | — | — | — | 1.25 | — | — | 0.45 | — |
| Texapon ® N70 Sodium lauryl ether sulfate + 2 EO | — | — | — | — | — | — | — | 2.7 |
| Glycerin | 5 | 5 | 5 | 5 | 5 | 5 | 5 | 5 |
| Benzoic acid | 0.5 | 0.5 | 0.5 | 0.5 | 0.5 | 0.5 | 0.5 | 0.5 |
| Water | | | | | to 100 | | | |
| Ratio by weight a:b | 4:1 | 5:1 | 5:1 | 6:1 | 10:1 | 13:1 | 10:1 | 5:1 |
| Viscosity | 4000 | 3000 | 3500 | 4000 | 9000 | 3500 | 11000 | 16000 |
| Particle size distribution | | | | | | | | |
| <15 μm | 99.9 | 98 | 98 | 99.9 | 83 | 89 | 85 | 91 |
| 15–20 μm | 0.1 | 2 | 2 | 0.1 | 8.1 | 7 | 9 | 5 |
| >20 μm | — | — | — | — | 8.8 | 4 | 6 | 4 |
| Mean particle diameter | 9.5 | 8 | 6.5 | 5.6 | 19 | 13 | 18 | 14 |

The invention claimed is:

1. An emulsifier mixture for a wax-based opacifier comprising:
   (a) an alkyl and/or alkenyl oligoglycoside;
   (b) a fatty acid partial glyceride; and
   (c) at least one betaine compound of formula (IV)

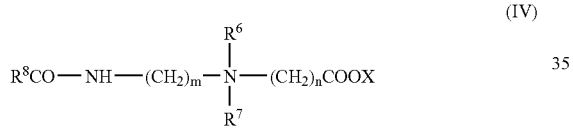

$$R^8CO-NH-(CH_2)_m-\underset{\underset{R^7}{|}}{\overset{\overset{R^6}{|}}{N}}-(CH_2)_nCOOX \quad (IV)$$

wherein $R^8CO$ is an aliphatic acyl group having from 6 to 22 carbon atoms and 0 or 1 to 3 double bonds, m is a number from 1 to 3, $R^6$ is hydrogen or an alkyl group having from 1 to 4 carbon atoms, $R^7$ is an alkyl group having from 1 to 4 carbon atoms, n is a number from 1 to 6 and X is an alkali metal, alkaline earth metal or ammonium ion, with the proviso that the ratio by weight of (a) plus (c) to (b) is between 6:1 and 1.5:1 and wherein the composition is free from anionic surfactants.

2. The emulsifier mixture of claim 1 wherein the alkyl and/or alkenyl oligoglycoside is a compound of the formula (I):

$$R^1O-[G]_p \quad (I)$$

wherein $R^1$ is an alkyl and/or alkenyl group having from 4 to 22 carbon atoms, G is a sugar unit having from 5 or 6 carbon atoms and p is a number from 1 to 10.

3. The emulsifier mixture of claim 1 wherein the fatty acid partial glyceride is a compound of the formula (II):

$$\begin{array}{l} CH_2O(CH_2CH_2O)_mCOR^2 \\ | \\ CHO(CH_2CH_2O)_nR^3 \\ | \\ CH_2O(CH_2CH_2O)_pR^4 \end{array} \quad (II)$$

wherein $R^2CO$ is a linear or branched, saturated and/or unsaturated acyl group having from 6 to 22 carbon atoms, each of $R^3$ and $R^4$ is independently the same as $R^2CO$ or OH, and wherein the sum (m+n+p) is 0 or a number from 1 to 100, with the proviso that at least one of $R^3$ and $R^4$ is OH.

4. The emulsifier mixture of claim 1 wherein the weight ratio of (a) plus (c) to (b) is from 2:1 to 3:1.

5. An opacifier composition comprising: (1) a wax;
   (2) an emulsifier mixture comprising:
   (a) an alkyl and/or alkenyl oligoglycoside;
   (b) a fatty acid partial glyceride; and
   (c) at least one betaine compound of formula (IV)

$$R^8CO-NH-(CH_2)_m-\underset{\underset{R^7}{|}}{\overset{\overset{R^6}{|}}{N}}-(CH_2)_nCOOX \quad (IV)$$

wherein $R^8CO$ is an aliphatic acyl group having from 6 to 22 carbon atoms and 0 or 1 to 3 double bonds, m is a number from 1 to 3, $R^6$ is hydrogen or an alkyl group having from 1 to 4 carbon atoms, $R^7$ is an alkyl group having from 1 to 4 carbon atoms, n is a number from 1 to 6 and X is an alkali metak alkaline earth metal or ammonium ion, with the proviso that the ratio by weight of (a) plus (c) to (b) is between 6:1 and 1.5:1, and wherein the composition is free from anionic surfactants.

6. The composition of claim 5 wherein the alkyl and/or alkenyl oligoglycoside is a compound of the formula (I):

$$R^1O-[g]_p \quad (I)$$

wherein $R^1$ is an alkyl and/or alkenyl group having from 4 to 22 carbon atoms, G is a sugar unit having from 5 or 6 carbon atoms and p is a number from 1 to 10.

7. The composition of claim 5 wherein the fatty acid partial glyceride is a compound of the formula (II):

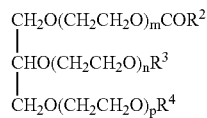

wherein R²CO is a linear or branched, saturated and/or unsaturated acyl group having from 6 to 22 carbon atoms, each of $R^3$ and $R^4$ is OH or independently the same as $R^2CO$ wherein the sum (m+n+p) is 0 or a number from 1 to 100, with the proviso that at least one of $R^3$ and $R^4$ is OH.

8. The composition of claim 5 wherein the weight ratio of (a) plus (c) to (b) is from 2:1 to 3:1.

9. The composition of claim 5 wherein the solids content is from 25 to 45% by weight, based on the final composition.

10. The composition of claim 5 wherein at least 90% of the composition has particle sizes below 10 μm.

* * * * *